United States Patent [19]

Garabedian

[11] Patent Number: Plant 7,075

[45] Date of Patent: Dec. 19, 1989

[54] PLUM TREE, "RANCHO CINCO"

[76] Inventor: John M. Garabedian, P.O. Box 7883, Fresno, Calif. 93747

[21] Appl. No.: 268,269

[22] Filed: Nov. 7, 1988

[51] Int. Cl.[4] ..... A01H 5/00

[52] U.S. Cl. ..... Plt./38

[58] Field of Search ..... Plt. 38

*Primary Examiner*—Robert E. Bagwill

*Attorney, Agent, or Firm*—Worrel & Worrel

[57] ABSTRACT

A new and distinct variety of Plum Tree denominated varietally as "Rancho Cinco" and which is characterized as to novelty by a date of maturity for commercial harvesting and shipment approximately August 6 through August 20 under the ecological conditions prevailing in Fresno, Calif. in the central part of the San Joaquin Valley of central California.

1 Drawing Sheet

BACKGROUND OF THE NEW VARIETY

The present invention relates to a new and distinct variety of Plum Tree, hereinafter denominated varietally as "Rancho Cinco", and more particularly to a plum tree which is somewhat broadly similar to the Westerner Plum Tree (U.S. Plant Pat. No. 5,609) and the Gar Fantasy Plum Tree (U.S. Plant Pat. No. 5,178) in its physical characteristics, but which is distinguished therefrom and characterized principally as to novelty by producing fruit which are ripe for commercial harvesting and shipment approximately on August 6 under the ecological conditions prevailing at Fresno, Fresno County, Calif., the subject variety maturing for harvesting and shipment approximately two or three weeks after the Westerner Plum Tree and approximately seven weeks before the Gar Fantasy Plum Tree. Further, the subject variety produces a semi-clingstone fruit which has a pleasing shape, and an attractive skin color.

The inventor has labored for decades in an effort to produce new and novel varieties of fruit trees. To develop these new varieties, the inventor has performed assorted activities including the selective cross breeding of trees having known and desired characteristics, the selective evaluation of chance seedlings from unknown parents, as well as routinely inspecting his several orchards in an effort to discover chance mutations of various types. The present variety of Plum Tree "Rancho Cinco" is an open-pollinated chance seedling of unknown parentage which was discovered within the cultivated area of the applicant's experimental block of trees which were growing on his Ranch No. 1 that is located at Kings Canyon and Fowler Avenues in Fresno, Calif.

ORIGIN AND ASEXUAL REPRODUCTION OF THE NEW VARIETY

The present variety of Plum Tree was discovered by the inventor as an open-pollinated seedling of unknown parentage growing within the cultivated area of his experimental block of trees on his Ranch No. 1 which is located at the corner of Fowler and Kings Canyon Avenues in Fresno, Fresno County, Calif. in 1975. The applicant noted the noteworthy characteristics of the subject variety and thereafter marked the chance seedling for subsequent observation. In the years which followed, the applicant evaluated the fruit produced by the new and novel variety of Plum Tree and in 1978 the inventor removed bud wood from the chance open-pollinated seedling and budded it onto mature test trees which were then growing on his Ranch No. 3 which is located along Belmont Avenue in Fresno, Calif. This first asexual reproduction resulted in progeny being produced which appear to have the same distinctive characteristics as the original chance open-pollinated seedling.

SUMMARY OF THE NEW VARIETY

The Rancho Cinco Plum Tree is characterized principally as to novelty by bearing fruit which are surprisingly similar in their overall physical characteristics to the Westerner Plum Tree (U.S. Plant Pat. No. 5,609) and the Gar Fantasy Plum Tree (U.S. Plant Pat. No. 5,178), but which is distinguished therefrom and characterized principally as to novelty by producing an attractively shaped dark red plum which is semi-freestone by nature and which is ripe for harvesting and shipment approximately two or three weeks after the Westerner Plum Tree (U.S. Plant Pat. No. 5,609) and approximately six or seven weeks before the Gar Fantasy Plum (U.S. Plant Pat. No. 5,178) under the present ecological conditions prevailing in Fresno County, Calif.

BRIEF DESCRIPTION OF THE DRAWINGS

The accompanying drawing is a color photograph of a characteristic twig bearing typical leaves, several mature fruit showing their external coloration sufficiently matured for harvesting and shipment, one fruit of the subject variety dissected in the axial plane to illustrate the flesh characteristics thereof, and several stones, all of the subject variety.

DETAILED DESCRIPTION

Referring more specifically to the pomological details of this new and distinct variety of Plum Tree, the following has been observed under the ecological conditions prevailing at the orchard of the inventor which is located in Fresno, Calif. All major color code designations are by reference to the Dictionary of Color by Maerz and Paul, Second Edition, 1950. Common color names are also employed occasionally.

TREE

Generally:

*Size.*—Large as compared with other common plum cultivars growing in the immediate geographical area.
*Vigor.*—Vigorous.
*Form.*—Upright, open, vase formed and tender.
*Productivity.*—Productive.
*Regularity of bearing.*—Regular.

Trunk:
*Shape.*—Stocky.
*Surface texture.*—Rough.

Branches:
*Size.*—Average as compared with other common plum cultivars.
*Surface texture.*—Shaggy.
*Color.*—Dull brown. The color is not particularly distinctive of the subject variety, however.
*Lenticels — Numbers.*—Numerous.
*Lenticels — Size.*—Small.

LEAVES

Size:
*Generally.*—Large.

Average length: Approximately 11.9 cm.
Average width: Approximately 5.2 cm.

Shape:
*Generally.*—Considered ovate, although occasionally elliptical shaped leaves may be found.

Leaf tip:
*Shape.*—Acuminate; although occasionally macronate forms may be located.

Leaf base:
*Shape.*—Acute.

Thickness: Average
Surface texture: Glabrous.

Color:
*Upwardly disposed surfaces.*—Dark green, (Plate 23, E-6, Page 69).
*Downwardly disposed surfaces.*—A pale green, (Plate 21, J-5, Page 65).

Marginal form: Considered finely serrate.

Petiole:
*Length.*—Average.
*Thickness.*—Medium.

Glands:
*Generally.*—No glands were evident.

FLOWER BUDS

Size: Considered small and short.
Form: Conic, plump, tender, and free.
Pubescence: Absent.

FLOWERS

Date of first bloom: In 1987, first bloom was observed on February 23.
Date of full bloom: In 1987, full bloom was observed on February 27.

Date of bloom:
*Generally.*—Considered early as compared with other common plum tree varieties. More particularly, the date of bloom is approximately two or three days after the Red Beaut Plum Tree and approximately the same time of the season as the Westerner Plum Tree under the current ecological conditions prevailing in Fresno, Calif.

Size:
*Generally.*—Small.

Petals:
*Color.*—White and having a slight salmon color. These colors are not particularly distinctive of the variety, however.

Calyx:
*Color.*—A light salmon color and occasionally a light pink color may be evident. These colors are not particularly distinctive of the variety, however.

FRUIT

Maturity when described: Ripe for harvesting and shipment approximately August 6 through as late as August 20 under the ecological conditions prevailing in Fresno, Calif.

Size:
*Generally.*—Variable, considered medium to large.

Average axial diameter: Approximately 60.5 mm.
Average diameter transverse and in the suture plane: Approximately 54 mm.
Average diameter transverse and at right angles to the suture plane: Approximately 57.4 mm.

Form:
*Uniformity.*—Symmetrically oblong and appearing nearly heart shaped. This shape is distinctive of the subject variety.

Suture:
*Generally.*—The suture appears as an inconspicuous line which extends from the base to the apex. The suture line, however, discontinues at the apex.

Ventral surface:
*Shape.*—Rounded slightly and lipped toward the base. The lips appear substantially equal.

Stem cavity — shape: Rounded, and flaring.
Stem cavity — depth: Approximately 6 mm.
Stem cavity — breadth: Approximately 7.8 mm.

Base:
*Shape.*—Rounded.

Apex:
*Shape.*—Rounded and truncate.

Pistil point:
*Position.*—Apical and appearing slightly pointed.

Skin:
*Thickness.*—Average.
*Surface texture.*—Glabrous and tender.
*Tenacious to flesh.*—Yes.
*Tendency to crack.*—Not observed in the dry season.
*Down.*—Quantity — wanting.
*Color.*—A dark burgundy red, (Plate 56, J-8).

Flesh:
*Color.*—A dark red, (Plate 54, H-10, Page 131).
*Surface of pit cavity.*—Color — Red. The color is substantially identical to the surrounding flesh color.
*Fibers.*—Generally — few in number, short, and tender.
*Amygdalin.*—Quantity — wanting.
*Juice production.*—Average.
*Texture.*—Soft, fine and melting at full commercial maturity.
*Fibers.*—Few and tender.
*Flavor.*—Considered mild and subacid.
*Aroma.*—Wanting.
*Eating quality.*—Good.

STONE

Attachment: The subject variety is considered semi-freestone by nature. More particularly, the stone adheres to the flesh over its entire surface.

Size:

*Generally.*—Average.

Average width: Approximately 22.6 mm.

Average breadth: Approximately 15 mm.

Average thickness: Approximately 9.5 mm.

Form:

*Generally.*—Elliptical.

Hilum:

*Shape.*—Narrow.

Sides:

*Generally.*—Equal.

Surface texture: Irregularly furrowed, especially near the base.

Ridges:

*Generally.*—The stone displays two prominent ridges along its ventral suture. Further, ridges appear on both sides and are considered to be interrupted.

Dorsal edge: A shallow narrow groove appears along the dorsal edge.

Stone:

*Color.*—Yellowish, (Plate 9, C-4).

Use: A fresh market dessert-type plum.

Keeping quality: Good.

Resistance to insects and diseases: Average as compared with other common plum cultivars.

Shipping quality: Good.

Although the new variety of Plum Tree possesses the described characteristics when grown under the ecological conditions prevailing in Fresno, Calif., in the central part of the San Joaquin Valley, it is to be understood that variations of the usual magnitude and characteristics incident to changes in growing conditions, fertilization, pruning and pest control are to be expected.

Having thus described and illustrated my new variety of Plum Tree, what is new and desired to be secured by Letters Patent is:

1. A new and distinct variety of Plum Tree substantially as illustrated and described and which produces fruit which are somewhat remotely similar to the fruit borne by the Westerner Plum Tree (U.S. Plant Pat. No. 5,609) and the Gar Fantasy Plum Tree (U.S. Plant Pat. No. 5,178), but which is distinguished therefrom, and characterized principally as to novelty by bearing semi-freestone fruit which are ripe for commercial harvesting and shipment approximately August 6 through August 20 under the ecological conditions prevailing in Fresno, Calif., the subject variety producing fruit which have a distinct oblong shape, a dark red flesh color and an excellent flavor.

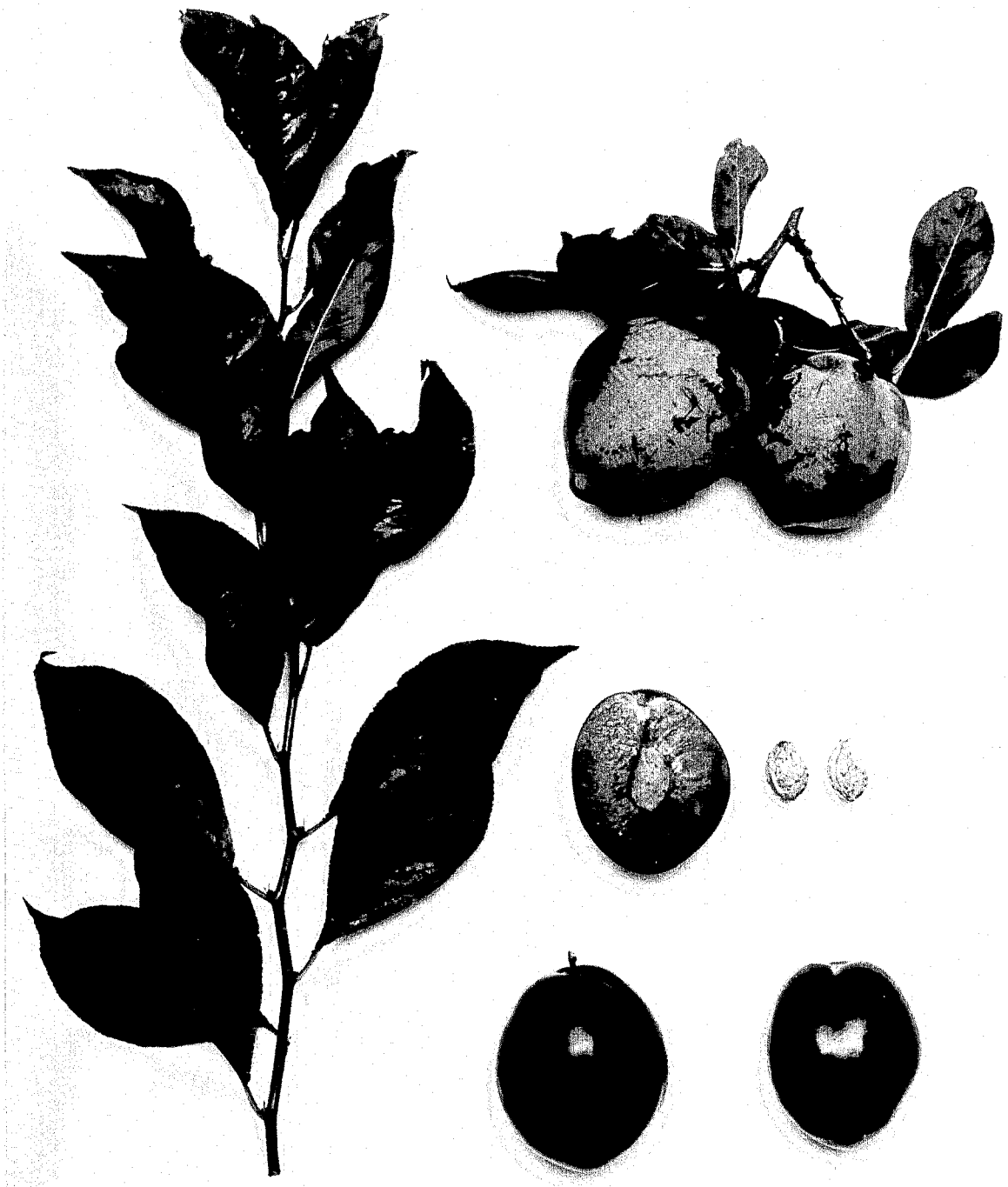

* * * * *